US012629441B2

(12) United States Patent
Kumar et al.

(10) Patent No.: US 12,629,441 B2
(45) Date of Patent: May 19, 2026

(54) DISINFECTING CAP FOR MALE AND FEMALE CONNECTORS

(71) Applicant: Becton, Dickinson and Company, Franklin Lakes, NJ (US)

(72) Inventors: Manish Kumar, Bengaluru (IN); Praveen Nalawade, Belagavi (IN); Shashwat Jain, Indore (IN); Kadamb Gupta, Greater Noida (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 648 days.

(21) Appl. No.: 17/979,214

(22) Filed: Nov. 2, 2022

(65) Prior Publication Data

US 2024/0139356 A1 May 2, 2024

(51) Int. Cl.
| | |
|---|---|
| *A61L 2/16* | (2006.01) |
| *A61M 39/20* | (2006.01) |
| *A61L 103/05* | (2026.01) |

(52) U.S. Cl.
CPC .............. *A61L 2/16* (2013.01); *A61M 39/20* (2013.01); *A61L 2103/05* (2026.01); *A61L 2202/121* (2013.01); *A61L 2202/15* (2013.01)

(58) Field of Classification Search
CPC ........ A61M 39/20; A61M 39/162; A61L 2/18
See application file for complete search history.

(56) References Cited

U.S. PATENT DOCUMENTS

| | | | |
|---|---|---|---|
| 8,172,825 | B2 | 5/2012 | Solomon et al. |
| 8,197,749 | B2 * | 6/2012 | Howlett .............. A61M 39/165 |
| | | | 604/905 |
| 8,671,496 | B2 | 3/2014 | Vaillancourt et al. |
| 8,696,820 | B2 | 4/2014 | Vaillancourt et al. |
| 8,740,864 | B2 | 6/2014 | Hoang et al. |
| 9,039,989 | B2 | 5/2015 | Liu et al. |
| 9,242,084 | B2 | 1/2016 | Solomon et al. |
| 9,283,369 | B2 | 3/2016 | Ma et al. |
| 9,352,140 | B2 | 5/2016 | Kerr et al. |
| 9,399,125 | B2 | 7/2016 | Burkholz |
| 9,480,833 | B2 | 11/2016 | Hoang et al. |
| D834,187 | S | 11/2018 | Ryan |
| 10,376,686 | B2 | 8/2019 | Burkholz et al. |
| 10,413,716 | B2 | 9/2019 | Sathe |
| 10,871,246 | B2 | 12/2020 | Marici et al. |
| 11,083,883 | B2 | 8/2021 | Ryan et al. |
| 11,273,298 | B2 | 3/2022 | Erekovcanski et al. |

(Continued)

*Primary Examiner* — Donald R Spamer
(74) *Attorney, Agent, or Firm* — Servilla Whitney LLC

(57) ABSTRACT

A cap configured to engage a male connector and a female connector includes a first housing for the female connector having a closed bottom, an open top, and a sidewall extending between the bottom and the top, and a first absorbent support disposed in the first housing configured to contact portions of the female connector. The cap also includes a removable second housing for the male connector disposed in the first housing. The second housing includes a bottom, a top, and a sidewall extending between the bottom and the top with an outer surface of the sidewall of the second housing engaged to an inner surface of the sidewall of the first housing. The cap also includes a second absorbent support disposed in the removable second housing configured to contact portions of the male connector.

17 Claims, 13 Drawing Sheets

(56)  References Cited

U.S. PATENT DOCUMENTS

| | | | |
|---|---|---|---|
| 11,344,715 B2 | 5/2022 | Erekovcanski et al. | |
| 11,353,147 B2 | 6/2022 | Marici et al. | |
| 11,389,636 B2 | 7/2022 | Coyle | |
| 2012/0210678 A1* | 8/2012 | Alcouloumre | A61B 17/3217 |
| | | | 206/370 |
| 2012/0302968 A1 | 11/2012 | Tennican | |
| 2012/0302997 A1* | 11/2012 | Gardner | A61M 39/20 |
| | | | 604/533 |
| 2013/0035667 A1 | 2/2013 | Anderson et al. | |
| 2013/0178804 A1 | 7/2013 | Tennican | |
| 2013/0197485 A1 | 8/2013 | Gardner et al. | |
| 2014/0135739 A1* | 5/2014 | Solomon | A61M 39/20 |
| | | | 604/535 |
| 2015/0005699 A1 | 1/2015 | Burbank et al. | |
| 2015/0086441 A1 | 3/2015 | She et al. | |
| 2016/0106968 A1* | 4/2016 | Solomon | A61M 39/165 |
| | | | 604/533 |
| 2016/0144118 A1 | 5/2016 | Solomon et al. | |
| 2016/0310720 A1 | 10/2016 | Solomon et al. | |
| 2018/0055962 A1 | 3/2018 | Drmanovic | |
| 2018/0064604 A1 | 3/2018 | Drmanovic | |
| 2018/0071508 A1 | 3/2018 | Drmanovic | |
| 2018/0085568 A1 | 3/2018 | Drmanovic | |
| 2018/0200500 A1 | 7/2018 | Ziebol et al. | |
| 2018/0214242 A1 | 8/2018 | Davis et al. | |
| 2018/0214684 A1 | 8/2018 | Avula et al. | |
| 2018/0250194 A1 | 9/2018 | Drmanovic | |
| 2018/0256804 A1 | 9/2018 | Burbank et al. | |
| 2018/0256880 A1 | 9/2018 | Follman et al. | |
| 2018/0256881 A1 | 9/2018 | Hitchcock et al. | |
| 2018/0256883 A1* | 9/2018 | Follman | A61M 39/162 |
| 2018/0369562 A1 | 12/2018 | Gardner et al. | |
| 2019/0038888 A1 | 2/2019 | Gardner | |
| 2019/0099593 A1 | 4/2019 | Avula et al. | |
| 2019/0117332 A1 | 4/2019 | Davis et al. | |
| 2019/0201681 A1 | 7/2019 | Ziebol et al. | |
| 2019/0262525 A1 | 8/2019 | Wyeth et al. | |
| 2019/0282795 A1 | 9/2019 | Fangrow | |
| 2019/0351212 A1 | 11/2019 | Dudar et al. | |
| 2020/0121858 A1 | 4/2020 | Anderson et al. | |
| 2020/0139037 A1 | 5/2020 | Ziebol et al. | |
| 2020/0155794 A1 | 5/2020 | Ziebol | |
| 2020/0197686 A1 | 6/2020 | Anderson et al. | |
| 2020/0238070 A1 | 7/2020 | Ryan | |
| 2021/0001110 A1 | 1/2021 | Bedoe et al. | |
| 2021/0093791 A1 | 4/2021 | Anderson et al. | |
| 2021/0275707 A1 | 9/2021 | Jiang et al. | |
| 2021/0322749 A1 | 10/2021 | Rothenberg et al. | |
| 2021/0322750 A1 | 10/2021 | Harandi et al. | |
| 2021/0322751 A1 | 10/2021 | Jiang et al. | |
| 2021/0322752 A1 | 10/2021 | Jiang et al. | |

* cited by examiner

DISINFECTING CAP FOR MALE AND FEMALE CONNECTORS

BACKGROUND OF THE INVENTION

Field of the Invention

The present disclosure relates generally to caps for medical connectors and, in particular, to a medical cap configured to be attached to either a male connector or a female connector for sealing, cleaning, and disinfecting portions of the connector.

Description of Related Art

Vascular access devices (VADs) are commonly used medical devices, which can include intravenous (IV) catheters, such as peripheral catheters or central venous catheters. If not properly maintained or if exposed to a non-sterile environment, the VADs can become contaminated, sealed with blood clots, and/or can spread infection. Further, bacteria and other microorganisms may gain entry into a patient's vascular system from access hubs, ports, or valves upon connection to the VAD to deliver a fluid or pharmaceutical to a patient. Therefore, each access hub (or port/valve or connection) configured for attachment to a VAD is associated with some risk of transmitting a catheter related bloodstream infection (CRBSI) to a patient.

Many medical facilities implement sterile practices and protocols to ensure that VADs and access hubs or ports are used properly and do not become sealed or infected. These protocols often include sterilizing the access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that access hubs, ports, and valves be capped with disinfection caps, when not in use, to prevent microbial ingress into the hub, port, or valve and to sterilize areas of the hub, port, or valve that contact the VAD. Disinfection caps are disposable cap devices that contain an amount of cleaning or disinfecting solution for sterilizing portions of the port, hub, and valve.

Access hubs and ports can have a variety of different types of male or female connectors for securing the hub or port to the VAD. Currently, practitioners often carry several types of caps with them so that they can cap the different types of hubs and ports that may be used for a particular patient. For example, caps for male needleless connectors and female needleless connectors, as well as intravenous (IV) and hemodialysis lines, use different connector designs and may require different caps. In particular, there can be "male disinfecting cap devices" for disinfecting ISO594-2 type of female threaded fluid luer connectors and "female disinfecting cap devices" for disinfecting ISO594-2 type of male threaded fluid luer connectors.

Some examples of universal caps that fit on both male and female connectors are known. For example, U.S. Pat. No. 10,871,246, entitled "Universal connector or cap for male and female threaded fittings," which is incorporated herein by reference in its entirety, discloses a cap including a threaded protrusion that can engage both a male connector and a female connector. However, there is a need for simpler cap designs, which can be manufactured inexpensively and efficiently. The universal caps of the present disclosure are configured to attach to both male and female medical connectors in a secure manner sufficient for preventing microbial ingress. Further, the universal caps of the present disclosure are configured to be easy to manufacture and assemble.

SUMMARY OF THE INVENTION

In accordance with an embodiment of the present invention, a cap configured to engage a male connector and a female connector having a first housing for the female connector having a closed bottom, an open top, and a sidewall extending between the bottom and the top; a first absorbent support disposed in the first housing configured to contact portions of the female connector; a removable second housing for the male connector disposed in the first housing, the second housing comprising a bottom, a top, and a sidewall extending between the bottom and the top with an outer surface of the sidewall of the second housing engaged to an inner surface of the sidewall of the first housing; and a second absorbent support disposed in the removable second housing configured to contact portions of the male connector.

In accordance with an embodiment of the present invention, the first housing is sized to engage the female connector to cover an opening of the female connector and the second housing is sized to engage the male connector to cover an opening of the male connector.

In accordance with an embodiment of the present invention, the cap is configured such that, following removal of the second housing from the first housing, the first housing is sized for the female connector to engage an inner surface of the first housing, thereby securing the first housing to the female connector.

In accordance with an embodiment of the present invention, the male connector includes a male luer connector having a stem configured to be inserted into the removable second housing, and wherein the second absorbent support is configured to clean and/or disinfect at least a distal tip of the stem.

In accordance with an embodiment of the present invention, the female connector includes a female luer connector comprising a threaded outer surface that engages the inner surface of the sidewall of the first housing, and wherein the first absorbent support is configured to clean and/or disinfect the threaded outer surface of the female luer connector.

In accordance with an embodiment of the present invention, the inner surface of the sidewall of the first housing includes threads that engage the threaded outer surface of the female luer connector.

In accordance with an embodiment of the present invention, the inner surface of the sidewall of the first housing includes threads, and wherein the second housing includes at least one protrusion extending radially outward from the sidewall of the second housing configured to engage the threads of the first housing to removably secure the second housing in the first housing.

In accordance with an embodiment of the present invention, the first housing and/or the second housing include single-molded parts, comprising a rigid thermoplastic polymer having at least one of polyester, polycarbonate, polypropylene, polyethylene, polyethylene terephthalate, or acrylonitrile butadiene styrene.

In accordance with an embodiment of the present invention, the first absorbent support and/or the second absorbent support includes sponges and/or an open cell foam, such as a porous foam having a thermoplastic elastomer.

In accordance with an embodiment of the present invention, a cleaning or disinfecting solution is absorbed by at least one of the first absorbent support and/or the second absorbent support, wherein the cleaning or disinfecting solution includes Isopropyl Alcohol (IPA).

In accordance with an embodiment of the present invention, the cleaning solution includes from about 0.5% to about 3.5% chlorhexidine gluconate and about 70% IPA.

In accordance with an embodiment of the present invention, when removably inserted in the first housing, the second housing compresses the first absorbent support, such that when the second housing is removed from the first housing, a first cleaner extends towards the open top of the first housing.

In accordance with an embodiment of the present invention, a seal is disposed in the second housing between the second absorbent support and the top of the second housing.

In accordance with an embodiment of the present invention, the seal includes a thermoplastic elastomer, such as a closed cell foam formed from the thermoplastic elastomer.

In accordance with an embodiment of the present invention, a protective cover is provided over the open top of the first housing.

In accordance with an embodiment of the present invention, the protective cover is attached to the first housing by heat sealing.

In accordance with an embodiment of the present invention, the protective cover includes an open bottom, a top, and a sidewall extending between the bottom and the top.

In accordance with an embodiment of the present invention, when connected to the first housing, the removable second housing extends through the open top of the first housing, such that a portion of the second housing is disposed within a space defined by the sidewall of the cover.

In accordance with an embodiment of the present invention, the sidewall of the cover is taped toward the top of the cover.

In accordance with an embodiment of the present invention, the bottom of the cover includes a flange and wherein a bottom surface of the flange is sealed to the first housing.

DESCRIPTION OF THE INVENTION

Figure 1B:
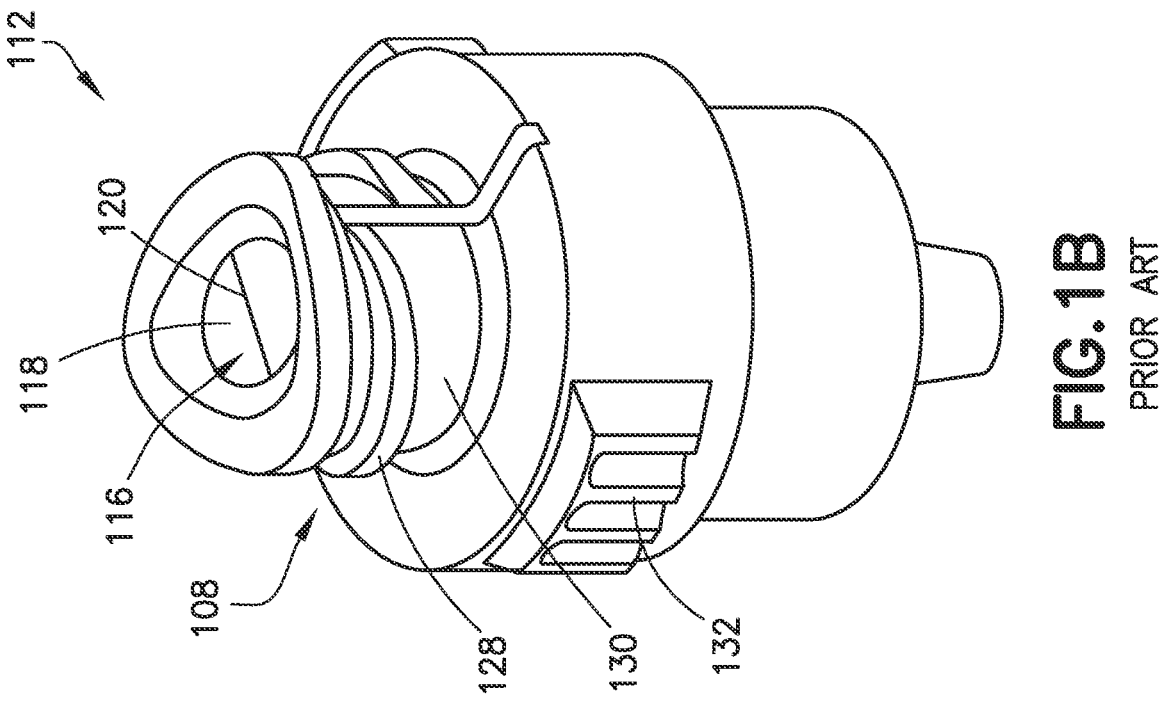
FIG. 1B is an example of a female connector including a septum with a slit, as is known in the prior art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 1A:
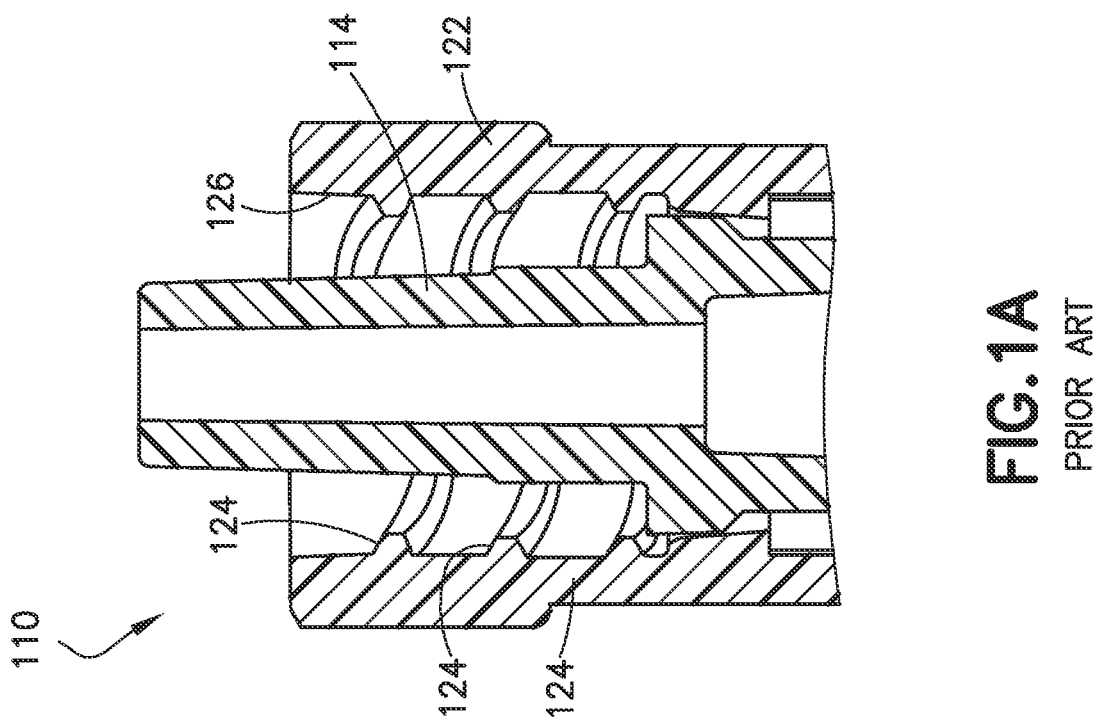
FIG. 1A is a cross-sectional view of an exemplary male connector, as is known in the prior art.

The present disclosure is directed to a cap 10, 210 configured to be connected to a medical connector 110, 112, such as an access hub, port, or valve for a VAD, to prevent the connector, port, or VAD from being contaminated by, for example, microbes, debris, or other contaminants. In some examples, the cap 10 can be configured to clean or disinfect the connector 110, 112 or port, ensuring that the connector 110, 112 or port remains sterile prior to use. The cap 10, 210 can be configured to remain in place on a connector 110, 112 or port for at least seven days, which is a maximum time of recommended use permitted by many medical facility sterile practice guidelines. The cap 10 can be configured to engage or be connected to different sizes, configurations, or types of medical connectors 110, 112. For example, the cap 10, 210 can be configured to engage or be connected to both a male connector 110 and a female connector 112. As used herein, a "male connector" refers to a connector 110 comprising an elongated member, such as a tubular member or stem 114, configured to be inserted in a tube or opening having an inner diameter that is larger than an outermost diameter of the male connector 110. An exemplary male connector 110 is shown in FIG. 1A. A "female connector" refers to a connector 112 comprising an opening or port 116 that is configured to receive an elongated member or tubular member of another object or device in order to connect the object or device to the female connector 112. The female connector 112 can comprise an elongated distal end portion 108 with a cover or septum 118 over the opening 116. An exemplary female connector 112 including a septum 118 with a slit 120 is shown in FIG. 1B.

In some examples, the cap 10 of the present disclosure is configured to engage both a male luer connector 110 and a female luer connector 112. For example, the cap 10 can be an appropriate size to receive a female luer connector 112 having an outer diameter of about 7.0 mm to about 8.0 mm. The cap 10, 210 can also be sized to receive a male luer connector 110 having an outer diameter of from about 8.0 mm to about 12.0 mm.

As used herein, a "luer connector" refers to a connector that includes a tapered portion (i.e., a luer taper) for creating a friction engagement between a tapered stem 114 or elongated member of a male luer connector 110 and a tapered cavity. Specifically, the male luer connector 110 includes a tapered stem 114 or elongated member having a tapered outer surface. The female luer connector 112 can include a tapered cavity configured to receive and engage the tapered stem 114 or elongated member to connect the male luer connector 110 to the female luer connector 112.

In order to secure the male and female connectors 110, 112 together, in some examples, the connectors 110, 112 can include engaging structures, such as threads, for drawing the connectors 110, 112 together. For example, as shown in FIG. 1A, the male luer connector 110 can include an annular shield 122 extending about the tapered stem 114 or elongated member. The annular shield 122 can include threads 124 on an inner surface 126 of the shield 122 configured to engage corresponding threads 128 on an outer surface 130 of the female luer connector 112. For example, as shown in FIG. 1B, the female luer connector 112 includes the threads 128 extending from the outer surface 130 positioned to engage the threads 124 on the inner surface 126 of the annular shield 122 of the male luer connector 110. Twisting the female connector 112 relative to the male connector 110 causes the corresponding threads 124, 128 to engage, which draws the connectors 110, 112 together, such that the tapered stem 114 or elongated member of the male luer connector 110 moves through the opening 116 of the female connector 112. In some examples, the female connector 112 can also include vertical ribs 132 near a proximal end of the female connector 112, which can be used to manipulate the female connector 112 making it easier to twist the female connector 112 relative to another connector or device. As previously described, the caps 10, 210 of the present disclosure are configured to cover both the male luer connector 110 (shown in FIG. 1A) and the female luer connector 112 (shown in FIG. 1B).

The caps 10, 210 of the present disclosure are configured to engage a variety of different configurations and orientations of medical connectors 110, 112, such as the previously described male and female needleless luer connectors. As will be appreciated by those skilled in the art, there are numerous different commercially available medical devices, such as hubs, ports, and valves, which include different variations of male or female connectors 110, 112. The cap 10 of the present disclosure is configured to adapt or deform so that it can be secured to numerous different types and sizes of connectors 110, 112. For example, as previously described, the caps 10 of the present disclosure are configured to attach to both male and female luer connectors 110, 112, such as male or female Luer-Lok™ connectors by Becton Dickinson and Company. The caps 10 of the present disclosure are also configured to cover different connector designs including, without limitation, the BD Q-Syte™, BD MaxZero™, BD MaxPlus™, and SmartSite™ needle free connectors by Becton Dickinson and Company. The caps 10 can also be configured to be connected to male and/or female connectors by other manufactures including, without limitation, MicroClave® connectors (ICU Medical Inc.) and Ultrasite® connectors (B. Braun Medical Inc.). In other examples, the cap 10 can be configured to be connect to one or more of the following commercially available male connectors: Kendall 2001NP; BD MP5303-C; ICU Med 12664-28; RyMed RYM-5307HPU; B. Braun 470108; Baxter 2C8537; Kawasumi B/-0094; Zyno B2-70071-D; B. Braun 470124; Baxter 2C7462; and Smith's Medical 536035.

FIGS. 2A-3C illustrate an exemplary cap 10 configured to engage and/or to be connected to either the male connector 110 or the female connector 112. The cap 10 is based on a cap-in-cap design, in which a single pre-packaged cap or cap assembly, such as the packaged cap shown in FIGS. 2A and 2B, includes a cap for the male connector 110 and a separate cap for the female connector 112, along with components, such as sponges, abrasive surfaces, and/or cleaning or disinfecting solutions, for cleaning, scrubbing, and disinfecting portions of the male and female connectors 110, 112. The cap 10 comprises a first or outer housing 12 that includes a closed bottom 14, an open top 16, and a sidewall 18 extending between the bottom 14 and the top 16. The outer housing 12 functions as the cap for the female connector 116 and, accordingly, is sized to engage the female connector to cover an opening or fluid port of the female connector 112. In particular, the outer housing 12 can be configured to cover portions of the female connector 112 including the distal end portion 108, opening 116, and septum 118.

Figures 2A, 2B:
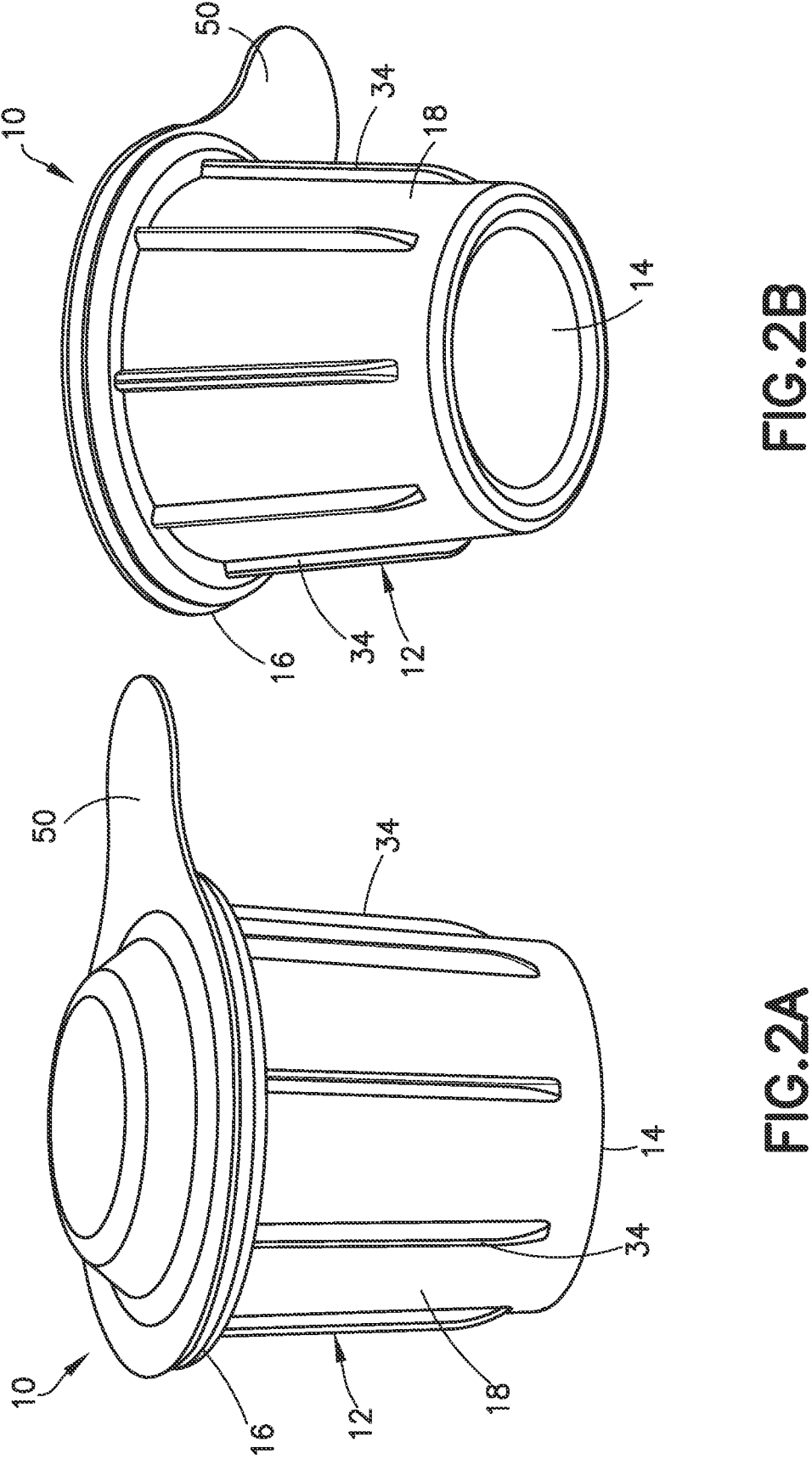
FIGS. 2A and 2B are perspective views of a cap for male and female connectors, according to an aspect of the present disclosure.
Figure 2C:
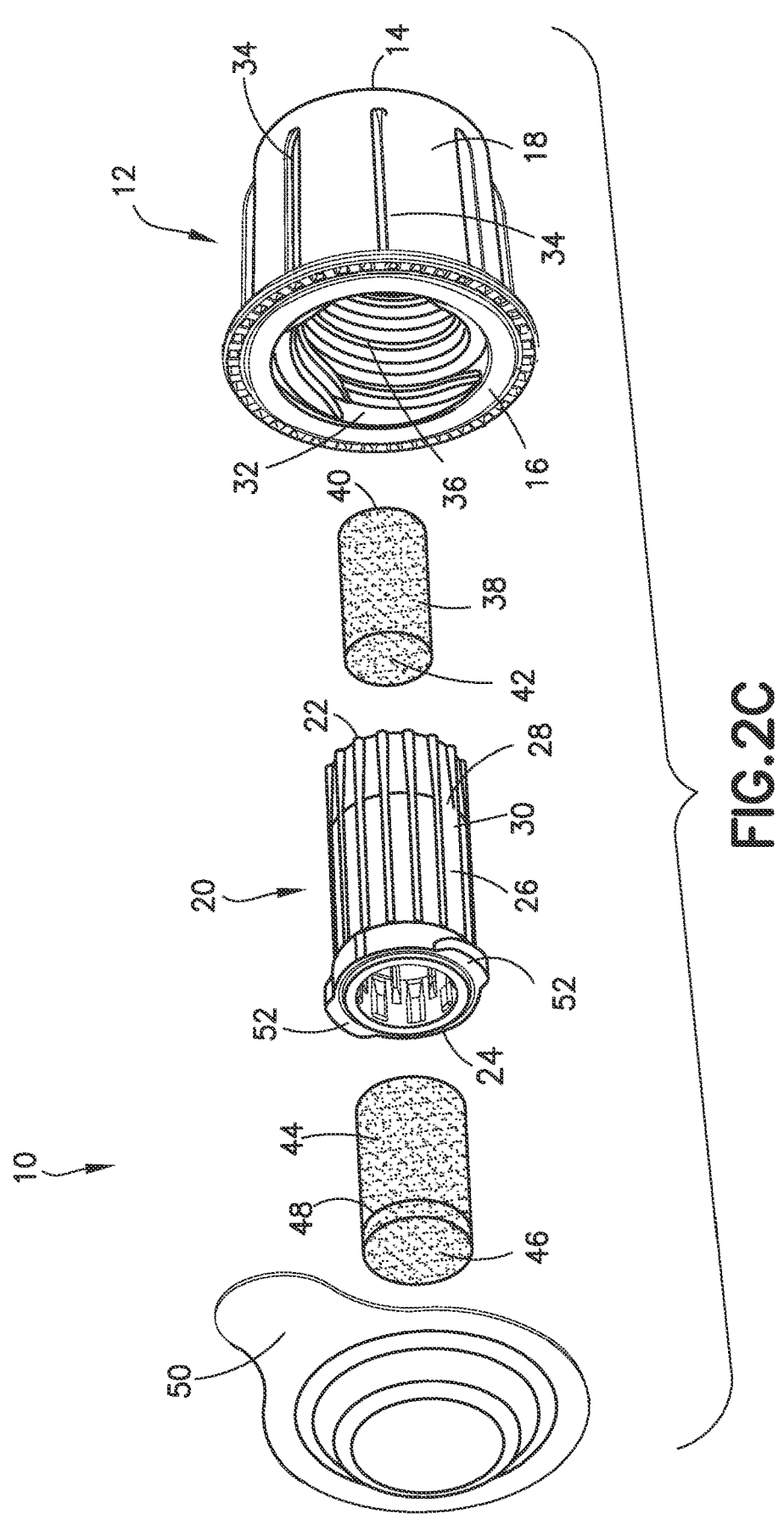
FIG. 2C is an exploded perspective view of the cap of FIGS. 2A and 2B.
Figure 2D:
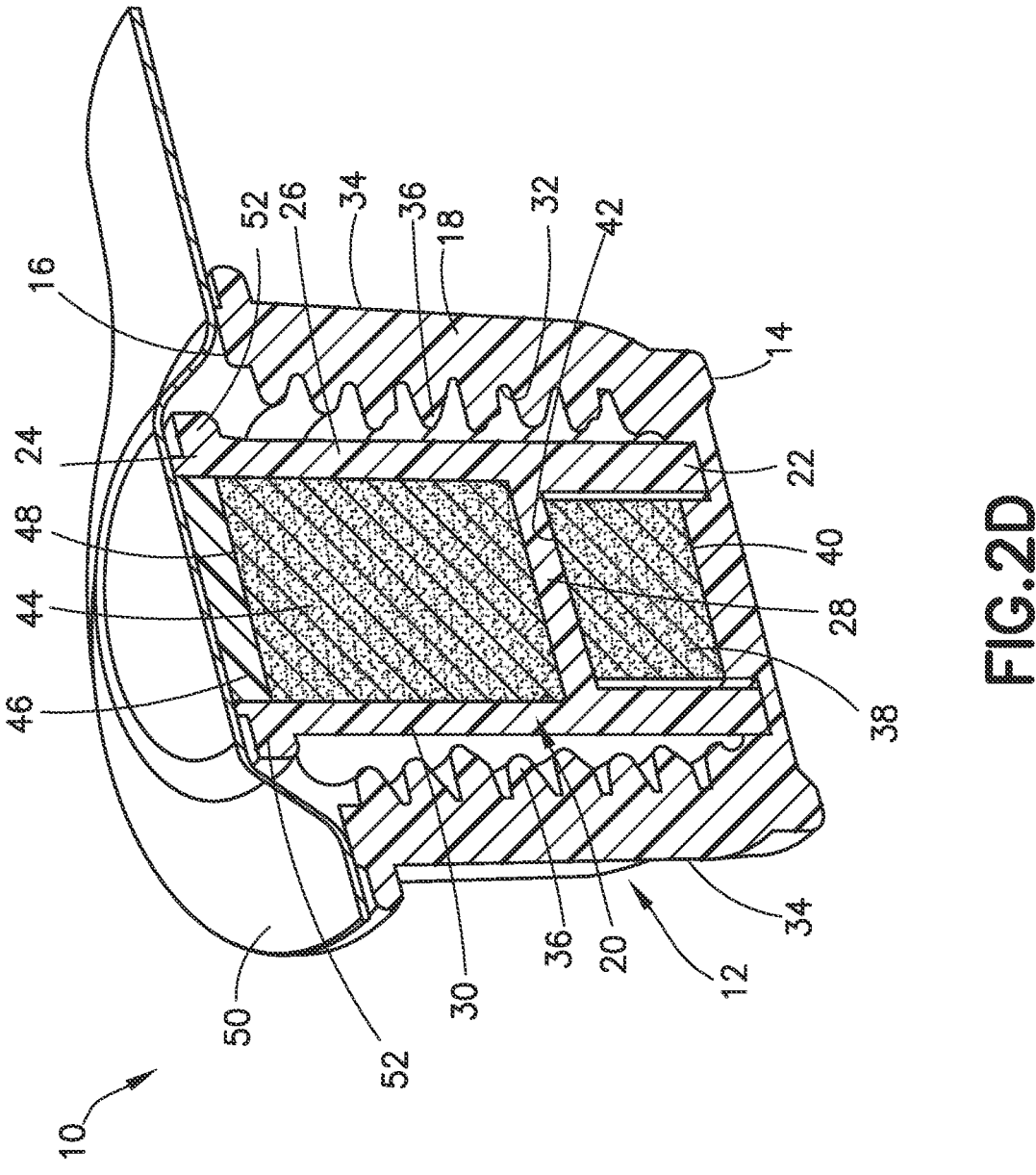
FIG. 2D is a cross-sectional view of the cap of FIGS. 2A and 2B.

The cap 10 further comprises a removable second or inner housing 20, which is configured to be a cap for the male connector 110. The inner housing 20 comprises a bottom 22, a top 24, and a sidewall 26 extending between the bottom 22 and the top 24. As shown in FIGS. 2B and 2C, the inner housing 20 and the outer housing 12 can be generally tubular or cup shaped containers. The inner housing 20 is sized to engage, cover, and seal the male connector 110. The outer housing 12 is sized to engage, cover, and seal the female connector 112. For example the outer housing 12 can be a cup shaped structure formed from an inexpensive material, such as a rigid plastic, which can be disposed of after a single use. In some examples, the outer housing 12 can include axial ridges 34 or similar supporting structures for increasing rigidity or structural integrity of the outer housing 12. The inner housing 20 can be a tubular structure, in which the top 24 and the bottom 22 are open. The inner housing 20 can further comprise a wall 28 extending across the sidewall 26. When the inner housing 20 is inserted into the outer housing 12, as shown in FIG. 2D, an outer surface 30 of the sidewall 26 of the inner housing 20 can be in contact with and/or engaged to an inner surface 32 of the sidewall 18 of the outer housing 12 to prevent the inner housing 20 from being prematurely removed from the outer housing 12.

The inner housing 20 can be sized to engage, cover, and seal an opening or fluid port of a male connector 110, such as a male luer connector. For example, as previously described, the male luer connector 110 can include a stem 114. The inner housing 20 can be sized to permit the stem 114 of the male luer connector to be inserted through the open top 24 of the inner housing 20, thereby engaging the male luer connector 110 to the inner housing 20. The male luer connector 110 can also include the annular shield 122 that surrounds the stem 114. The inner housing 20 can be sized to fit within the annular shield 122 of the male connector 110, such that the shield 122 does not prevent the inner housing 20 from being attached to and sealing the stem 114. Once the male luer connector 110 is connected to the inner housing 20, the inner housing 20 can be removed from the outer housing 12. Once the inner housing 20 is removed, the outer housing 12 can be discarded.

By contrast, in order to connect the outer housing 12 to the female connector 112, a practitioner first removes the inner housing 20 from the outer housing 12 by pulling the inner housing 20 away from the outer housing 12. The inner housing 20 can then be discarded. After the inner housing 20 is removed and discarded, the female connector 112 can be connected to the outer housing 12 by pressing the female connector 112 into the outer housing 12 and/or rotating the female connector 112 relative to the outer housing 12.

In some examples, the outer housing 12 can include threads 36 on the inner surface 30 of the outer housing 12. The threads 36 can be configured to engage corresponding threads 128 of the female connector 112 in order to secure the female connector 112 to the outer housing 12. In such examples, the outer surface 30 of the sidewall 26 of the inner housing 20 can also include protrusions 52, such as lugs or threads, configured to engage the threads 36 of the outer housing 12 to removably secure the inner housing 20 in the outer housing 12. In some examples, the inner housing 20 may be removed from the outer housing 12 by rotating the inner housing 12 in order to release the projection or lug from the threads 36 of the outer housing 12. In other examples, the inner housing 20 can be held or retained within the outer housing 12 by other mechanical connectors or engagements, such as by friction, an interference engagement, or by clips, brackets, snaps, or other removable connectors, as are known in the art. In that case, the inner housing 20 can be removed from the outer housing 12 by pulling the inner housing 20 away from the outer housing 12, as shown by arrow A1 in FIG. 3A, with sufficient force to overcome the engagement or connection between the inner housing 20 and the outer housing 12.

In some examples, the outer housing 12 and the inner housing 20 of the cap 10 are separately molded parts formed by injection molding or other molding processes known in the art. The separately molded housings 12, 20 can be assembled together prior to packaging the cap 10 for transport. The housings 12, 20 can be formed from a thermoplastic polymer material, such as polyester, polycarbonate, polypropylene, polyethylene, polyethylene terephthalate, or acrylonitrile butadiene styrene. In some examples, the housings 12, 20 can be formed from a durable material, such as a material having a shore hardness D value of less than or equal to 95 (Shore D). Alternatively, the housings 12, 20 can be formed from a more flexible material, such as a material having a shore hardness A value less than or equal to 130 (Shore A).

The cap 10 also includes absorbent members or support structures (referred to herein as absorbent supports) for cleaning and disinfecting portions of the male and female connectors 110, 112. In particular, absorbent supports can be configured to clean and disinfect surfaces of the stem 114 and shield 122 of the male connector 110. The absorbent supports can also be configured to clean and disinfect portions of the distal end portion 108, opening or port 116, and septum 118 of the female connector 112. For example, as shown in FIGS. 2C and 2D, the cap 10 can include a first or outer absorbent support 38 disposed in the inner housing 20 configured to contact portions of the female connector 112. As shown in FIG. 2D, the outer absorbent support 38 can be a cylindrical member having a bottom surface 40 proximate to the bottom 14 of the outer housing 12. The inner housing 20 can contact and compress the outer absorbent support 38. When the inner housing 20 is removed from the outer housing 12, the outer absorbent support 38 can expand, such that a top surface 42 of the outer absorbent support 38 extends towards the open top 16 of the outer housing 12. In some examples, the outer absorbent support 38 can be configured to contact portions of the female connector 112 in order to clean and/or disinfect portions of the female connector 112. For example, the outer absorbent support 38 can be configured to clean and/or disinfect the distal end portion 108, septum 118, and slit 120 of the female connector 112.

The cap 10 can also include a second or inner absorbent support 44, which can be disposed in the removable inner housing 20 of the cap 10. The inner absorbent support 44 can be configured to contact portions of the male connector 110 in order to clean and/or disinfect the portions of the male connector 110. For example, the inner absorbent support 44 can be positioned to contact and clean a distal tip of the stem 114 of the male luer connector 110, which is sized to be inserted into the inner housing 20. The inner absorbent support 44 can be a cylindrical structure sized to fit within a space defined by the sidewall 26 of the inner housing 20. The inner absorbent support 44 is generally narrower than the outer absorbent support 38 and may also be shorter than the outer absorbent support 38. In some examples, the inner absorbent support 44 is in contact with and/or mounted to the wall 28 of the inner housing 20, as shown in FIG. 2D.

The absorbent supports 38, 44 can be held within cylindrical interior spaces or cavities of the inner housing 20 and the outer housing 12 by conventional adhesives or fasteners, as are known in the art. In other examples, the absorbent supports 38, 44 can be held in place in the inner housing 20 or the outer housing 12 by friction between the sidewalls 18, 26 of the housings 12, 20 and the absorbent supports 38, 44. In some examples, the absorbent supports 38, 44 are formed from an absorbent material capable of absorbing a cleaning or disinfecting solution for cleaning and/or disinfecting portions of the male connector 110 and the female connector 112. For example, the absorbent supports 38, 44 can comprise a thermoplastic elastomer, such as polypropylene, polyethylene, or synthetic or natural rubber (e.g., isoprene).

The absorbent supports 38, 44 can also comprise a porous foam (e.g., an open cell foam) or sponge capable of absorbing the cleaning or disinfecting solution, such as a foam or sponge comprising polyurethane. In other examples, the foam material can be a Plastazote® foam, which is an engineered polymer foam by Zotefoams PCL. In some examples, a porosity of the absorbent supports 38, 44, which contacts the surfaces of the female connector 112, can be optimized so that the material is abrasive enough to scrub or mechanically remove objects from surfaces of the female connector 112, while, at the same time, limiting ingress of cleaning or disinfecting solution into portions of the female connector 112. Further, a height of the absorbent supports 38, 44 and/or amount of cleaning or disinfecting solution contained therein can be optimized for use with both short and tall connectors 110, 112. As used herein, a "short connector" refers to a connector that does not insert very far into the cap 10.

A "tall connector" refers to a connector that inserts into the cap 10 by a substantial distance, such that a distal end of the connector 110, 112 is proximate to the bottom 14, 22 of the outer housing 12 or the inner housing 20. In particular, the height of the absorbent supports 38, 44 and amount of cleaning or disinfecting solution contained therein should be large enough so that sufficient cleaning solution is released from the absorbent supports 38, 44 when the cap 10 is attached to a short connector to disinfect surfaces of the short connector. However, the height of the absorbent supports 38, 44 and amount of cleaning solution may be somewhat limited so that liquid ingress into a lumen of the connector 110, 112 does not occur when the cap 10 is attached to a taller connector.

The absorbent supports 38, 44 can be provided (i.e., presoaked) with the cleaning or disinfecting solution. For example, the cleaning or disinfecting solution can be an antimicrobial, anti-fungal, antibacterial, or antiviral solution that cleans and sterilizes surfaces of the connectors 110, 112. In some examples, the cleaning solution can be isopropyl alcohol (IPA), such as about 70% IPA. In other examples, the cleaning solution can be about 0.5% to about 3.5% chlorhexidine gluconate in combination with about 70% IPA. A chlorohexidine composition may be beneficial because it has a slower evaporation rate than IPA and, therefore, provides a more persistent disinfectant activity after the cap 10 is removed from the connector 110, 112 and before the VAD is connected to the hub, port, or valve.

In some examples, the cap 10 further comprises a seal 46 that covers the inner absorbent support 44. For example, as shown in FIG. 2D, the seal 46 can be positioned in the inner housing 20 over the inner absorbent support 44, specifically between a top surface 48 of the inner absorbent support 44 and the top 24 of the inner housing 20. The seal 46 can prevent fluids, such as cleaning or disinfecting solution in the cap 10, from flowing into the lumen of the male luer connector 110. In some examples, the seal 46 can be formed from a thermoplastic elastomer, such as a closed cell foam formed from the thermoplastic elastomer. Also, similar to the outer absorbent support 38, the seal 46 can comprise a porous material that is sufficiently abrasive to scrub or mechanically remove objects, such as microbes and other debris, from surfaces of the male connector 110.

With continued reference to FIGS. 2A-3C, the cap 10 can further comprise a removable and/or disposable protective cover 50. The protective cover 50 is positioned over the open top 16 of the outer housing 12. The protective cover 50 is provided to protect components and portions of the cap 10, such as the inner surface 32 of the outer housing 12, the inner housing 20, the seal 46, and the first and inner absorbent supports 38, 44. In particular, the protective cover 50 can protect the cap 10 during transport and storage to prevent contamination and to prevent the cleaning or disinfecting solution from evaporating prior to use. The protective cover 50 can comprise a sheet, such as a polymer film, with adhesive on a first side of the sheet for removably mounting the protective cover 50 to the open top 16 of the outer housing 12. Alternatively, the protective cover 50 can be removably mounted to the open top 16 of the outer housing 12 by heat sealing. The protective cover 50 can be formed from a material that is impervious or substantially impervious to air, so that the cleaning or disinfecting solution on the absorbent supports 38, 44 does not evaporate or dry-out prior to use of the cap 10. Accordingly, the protective cover 50 can increase a shelf life of the cap 10, as well as prevent microbes and other debris from collecting in the cap 10 prior to use.

Figure 3A:
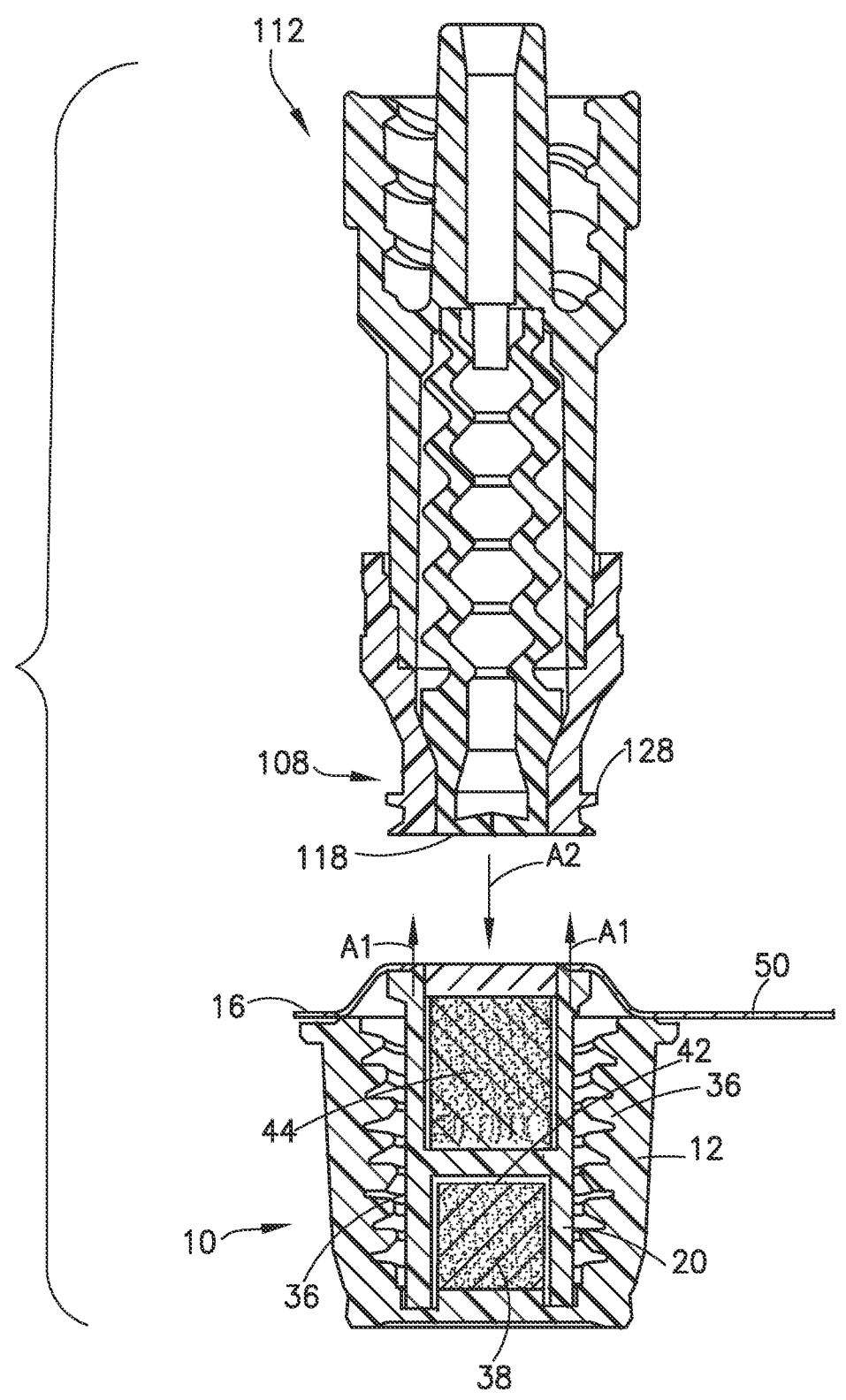
FIG. 3A is a cross-sectional view showing the cap of FIGS. 2A and 2B in an initial state prior to being connected to a female connector, according to an aspect of the present disclosure.
Figure 3B:
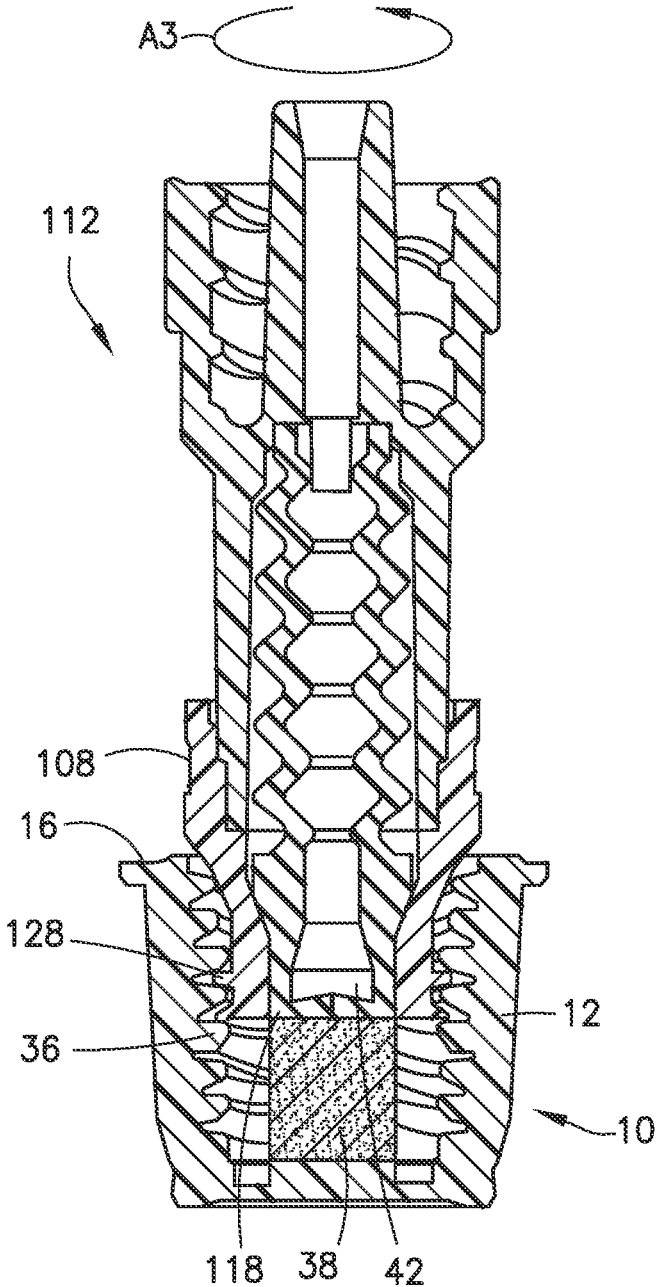
FIG. 3B is a cross-sectional view showing the cap of FIGS. 2A and 2B connected to a female connector, according to an aspect of the present disclosure.
Figure 3C:
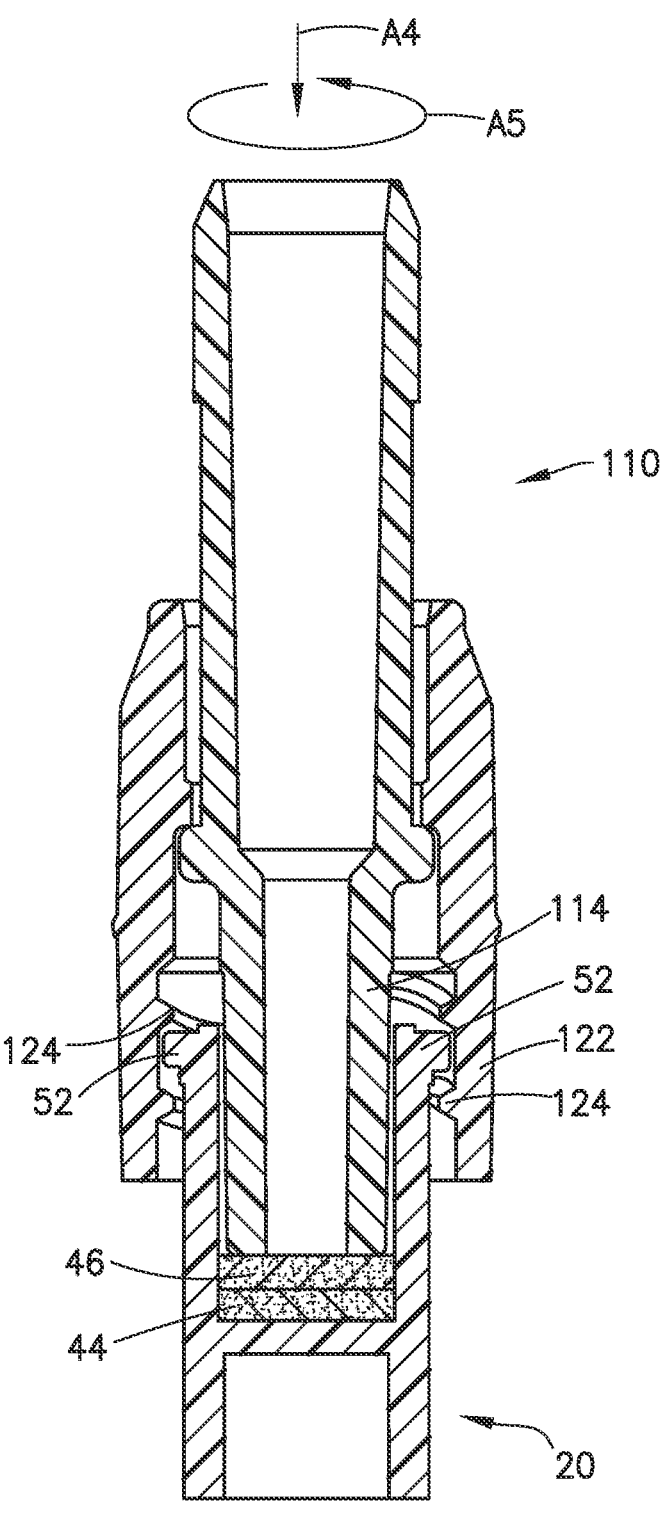
FIG. 3C is a cross-sectional view showing the cap of FIGS. 2A and 2B connected to a male connector, according to an aspect of the present disclosure.

In order to connect the cap 10 to a female connector 112, such as the female connector shown in FIGS. 3A and 3B, the practitioner first removes any packaging from the cap 10 and removes the protective cover 50 from the open top 16 of the outer housing 12. The practitioner then removes the inner housing 20 and inner absorbent support 44 contained therein from the outer housing 12, as shown by arrows A1 (in FIG. 3A). For example, the practitioner may grasp the inner housing 20 and pull the inner housing 20 axially away from the outer housing 12 with sufficient force to overcome any friction engagement, interference engagement, or mechanical connections between the inner housing 12 and the outer housing 20. Alternatively, in some examples, the practitioner may rotate the inner housing 12 relative to the outer housing 20 to cause screws, threads, lugs, or protrusions 52 of the inner housing 20 to disengage from threads 36 of the outer housing 12. The removed inner housing 20 can be discarded, if it is not used for covering a male connector 110. As previously described, removing the inner housing 20 from the outer housing 12 causes the outer absorbent support 38 to expand axially through the outer housing 12. The absorbent support 38 is shown in an expanded position in FIG. 3B.

Once the inner housing 20 is removed, the practitioner moves the female connector 112 toward the outer housing 12, as shown by arrow A2 in FIG. 3A, causing the corresponding threads 128 of the female connector 112 to contact the threads 36 of the outer housing 12. The practitioner then rotates the female connector 112 relative to the outer housing 12, as shown by arrow A3 in FIG. 3B, causing the distal end portion 108 of the female connector 112 to be drawn into the outer housing 12, as shown in FIG. 3B. Drawing the female connector 112 into the outer housing 12 causes the distal end portion 108 and septum 118 of the female connector 112 to contact the top surface 42 of the outer absorbent support 38, which may compress the outer absorbent support 38 releasing cleaning or disinfecting solution from the outer absorbent support 38. The cleaning or disinfecting solution contacts portions of the female connector 112, such as the distal end portion 108, septum 118, and threads 128 of the female connector 112 for cleaning and disinfecting the female connector 112. As previously described, contact between abrasive surfaces of the outer absorbent support 38 and surfaces of the female connector 112 may also mechanically remove microbes and other debris from the female connector 112, which contributes to the cleaning effect provided by the cap 10.

In order to remove the cap 10 from the female connector 112, the practitioner rotates the cap 10 in an opposite direction (i.e., an opposite direction of arrow A3 in FIG. 3B) causing threads 36 of the outer housing 12 to release from the threads 128 of the female connector 112. Once the threads 36, 128 are released, the practitioner can pull the outer housing 12 away from the female connector 112. Once the outer housing 12 is removed, a VAD can be connected to the hub, port, or valve through the female connector 112, as previously described.

In order to connect the cap 10 to a male connector 110 (shown in FIG. 3C), the practitioner first removes any packaging and the protective cover 50 from the cap 10. The practitioner then moves the male connector 110 in a direction of arrow A4 (shown in FIG. 3C), causing the stem 114 of the male connector 110 to be partially inserted into the inner housing 20 and bringing the distal tip of the stem 114 into contact with the seal 46 and/or with the inner absorbent support 44. Continuing to move the male connector 110 toward the inner housing 12 brings threads 124 of the annular shield 122 of the male connector 110 into contact with the protrusions 52 or lugs on the outer surface 30 of the inner housing 20. Once the protrusions 52 or lugs contact the threads 124, the practitioner can rotate the male connector 110 relative to the inner housing 20, as shown by arrow A5 in FIG. 3C, causing the stem 114 of the male connector 110 to be drawn farther into the inner housing 20, which causes the distal tip or end of the stem 114 to contact and compress the seal 46 and/or inner absorbent support 44.

As previously described, the contact between the male connector 110 and the seal 46 and/or the inner absorbent support 44 can release cleaning solution, causing the cleaning solution to contact and sterilize surfaces of the male connector 110. In particular, the cleaning solution can contact an outer surface of the stem 114 for sterilizing the male connector 110. Cleaning solution may also contact the inner surface 126 and threads 124 of the annular shield 122 to clean and sterilize portions of the annular shield 122. Also, as previously described, direct contact between surfaces of the male connector 110 and abrasive portions of the seal 46 can mechanically remove microbes, debris, and other contaminants from surfaces of the male connector 110, contributing to the disinfecting effects provided by the cap 10.

Once the male connector 110 is secured to the inner housing 20 due to the engagement between the protrusions 52 or lugs of the inner housing 20 and the threads 124 of the annular shield 122, as well as an interference or friction engagement between an outer surface of the stem 114 and the inner surface of the sidewall 26 of the inner housing 20, the practitioner can remove the outer housing 12 from the inner housing 20 and male connector 110. For example, as previously described, the practitioner can pull the outer housing 12 axially away from the inner housing 20 with sufficient force to overcome any friction engagement, interference engagement, or mechanical connection between the inner housing 20 and the outer housing 12. Alternatively, in other examples, the practitioner can rotate the inner housing 20 relative to the outer housing 12 in order to release the threads 36 of the outer housing 12 from protrusions 52 or lugs of the inner housing 20. Once the outer housing 12 is removed, it can be discarded unless it is being used to connect to a female connector 112.

In order to remove the inner housing 20 from the male connector 110, the practitioner rotates the inner housing 20, causing the protrusions 52 or lugs of the inner housing 20 to release from the threads 124 of the annular shield 122. Once the threads 124 are released, the practitioner pulls the inner housing 20 away from the male connector 110 with sufficient force to overcome the interference and/or friction engagement between the male connector 110 and portions of the cap 10. Once the inner housing 20 is removed, a VAD can be connected to the hub, port, or valve through the male connector 110, as previously described.

FIGS. 4A-5C illustrate another example of a cap 210 configured to be engaged with and/or connected to either a male connector 110, such as a male luer connector, or to a female connector 112, such as a female luer connector. As in previous examples, the cap 210 of FIGS. 4A-5C includes the first or outer housing 212, which is configured to cover the female connector 112, and the second or inner housing 220, which is configured to cover the male connector 110. As in previous examples, the cap 210 also includes the outer absorbent support 238 disposed in the outer housing 212 configured to contact portions of the female connector 110 and the inner absorbent support 244 disposed in the removable inner housing 220 configured to contact portions of the male connector 110. As in previous examples, the inner housing 220 is engaged to the outer housing 212 by a friction engagement, interference engagement, or rotational engagement. For example, the inner housing 220 can include the protrusions 252 or lugs that engage threads 236 of the outer housing 212 for securing the inner housing 220 in the outer housing 212.

Figure 4A:
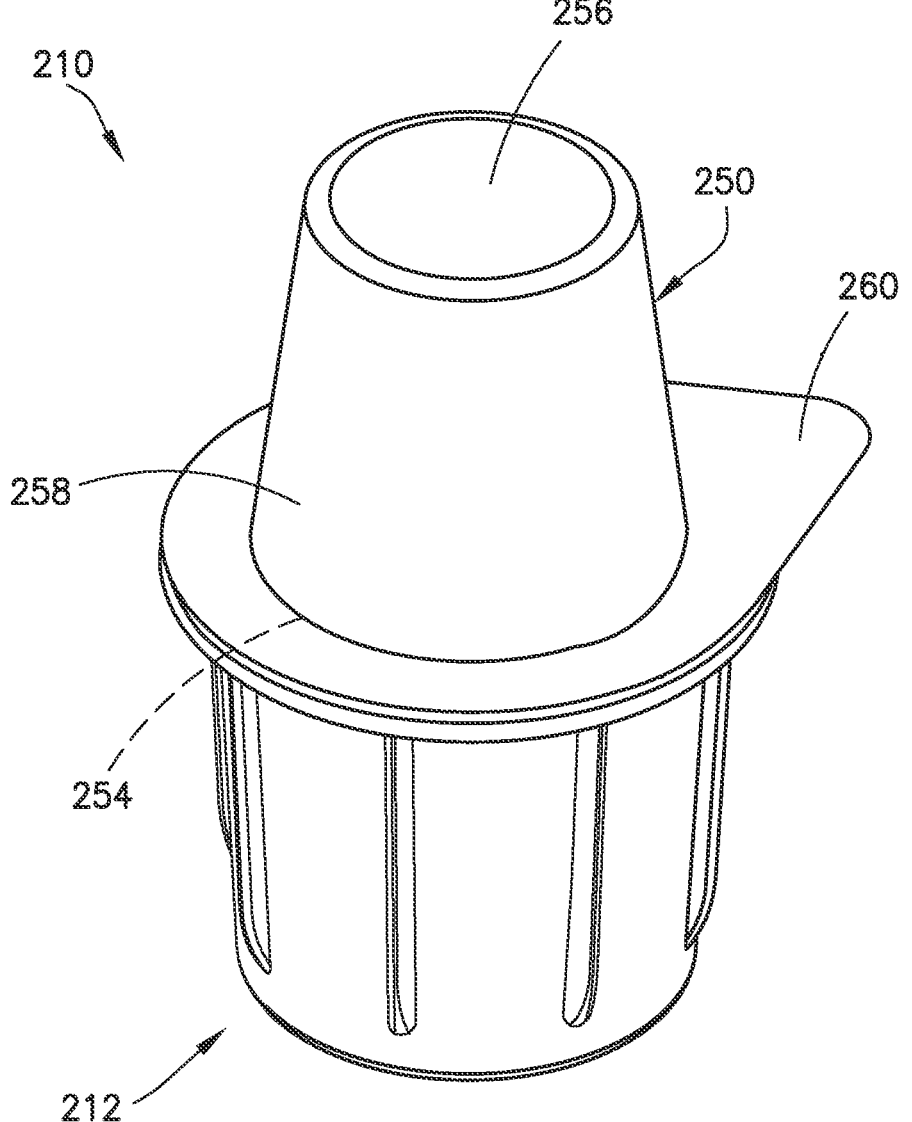
FIG. 4A is a perspective view of another example of a cap for male and female connectors, according to an aspect of the present disclosure.
Figure 4B:
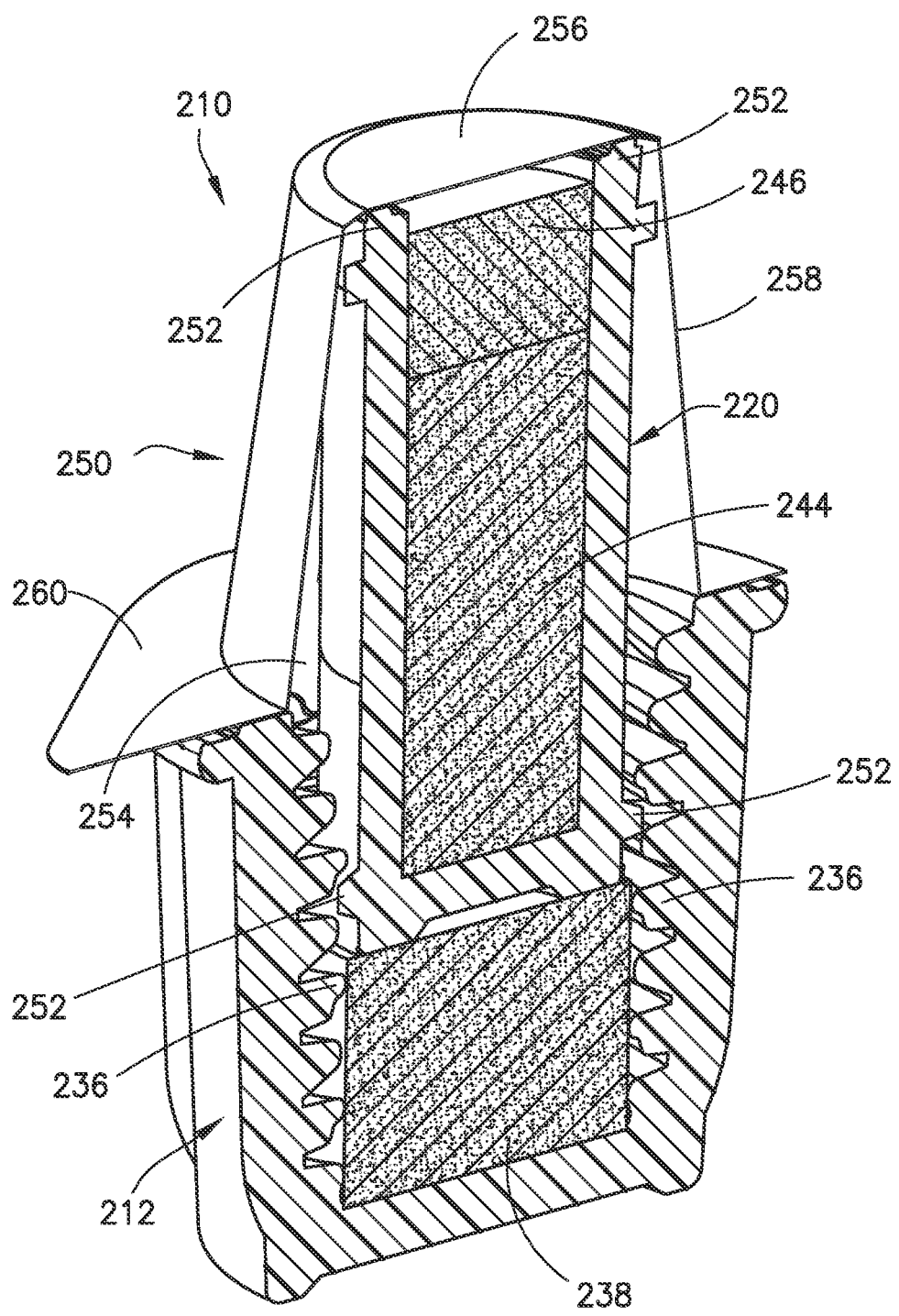
FIG. 4B is a cross-sectional view of the cap of FIG. 4A.
Figure 4C:
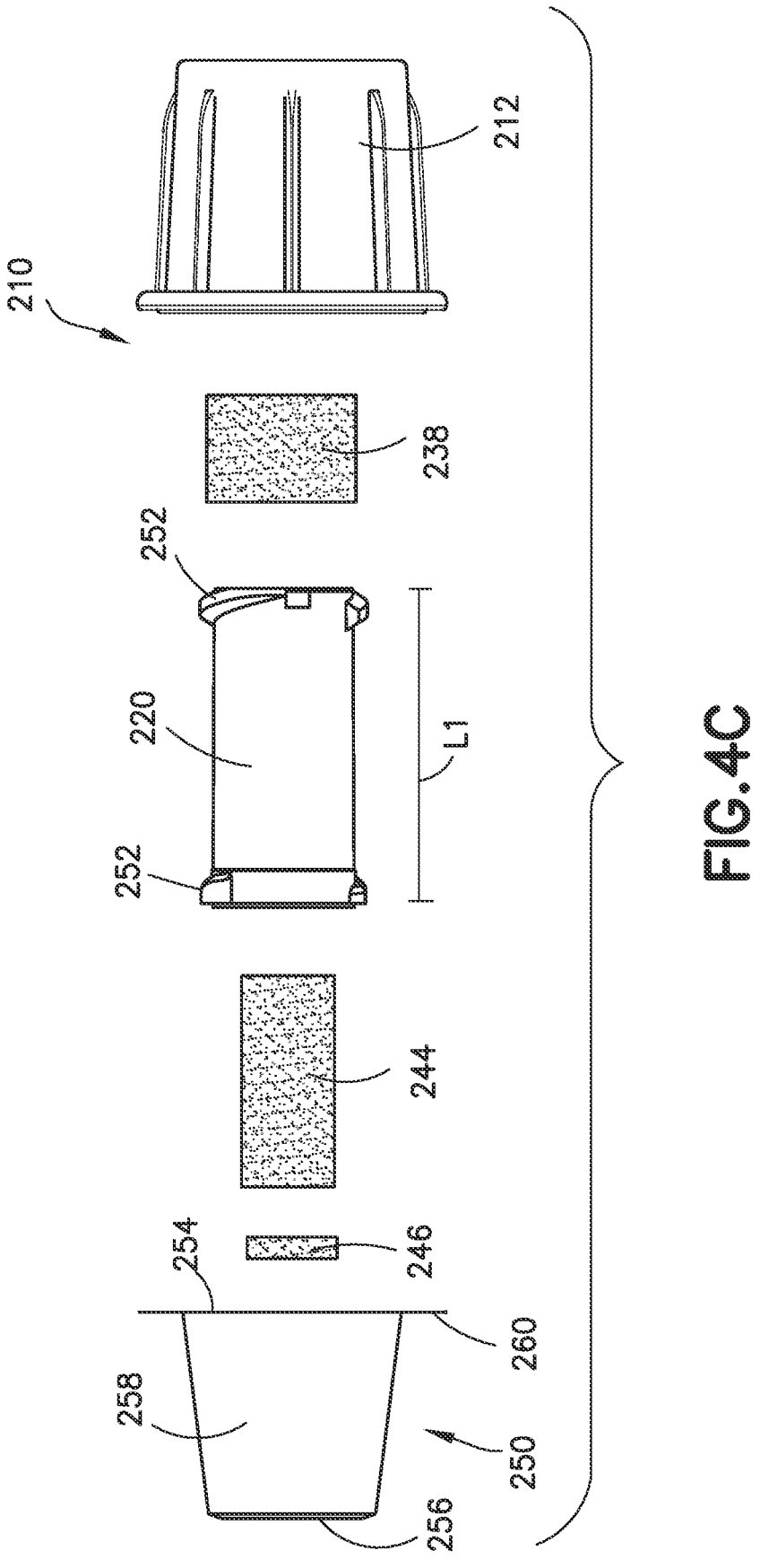
FIG. 4C is an exploded perspective view of the cap of FIG. 4A.
Figure 5A:
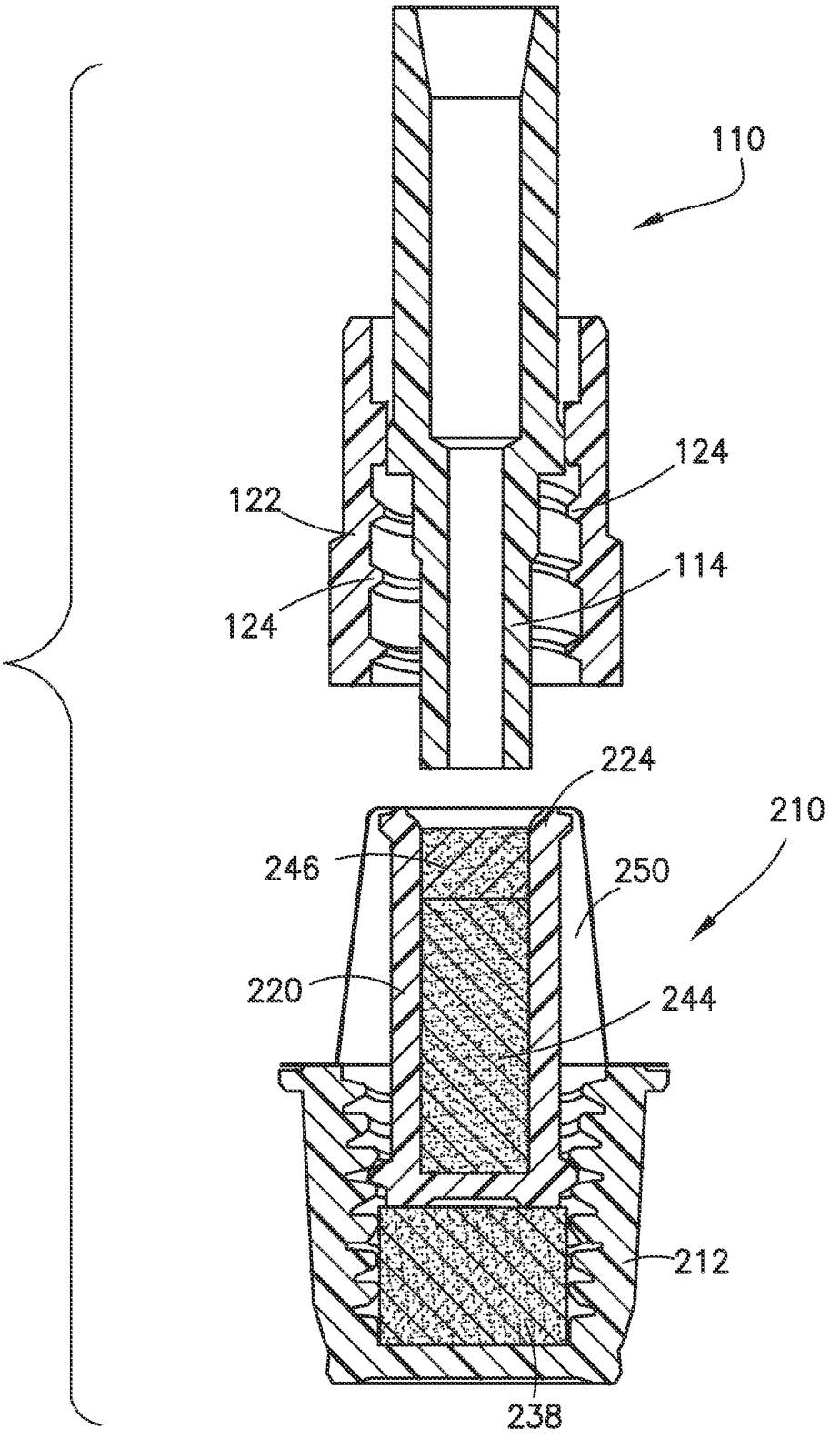
FIG. 5A is a cross-sectional view of the cap of FIG. 4A prior to being connected to a male connector, according to an aspect of the present disclosure.
Figure 5B:
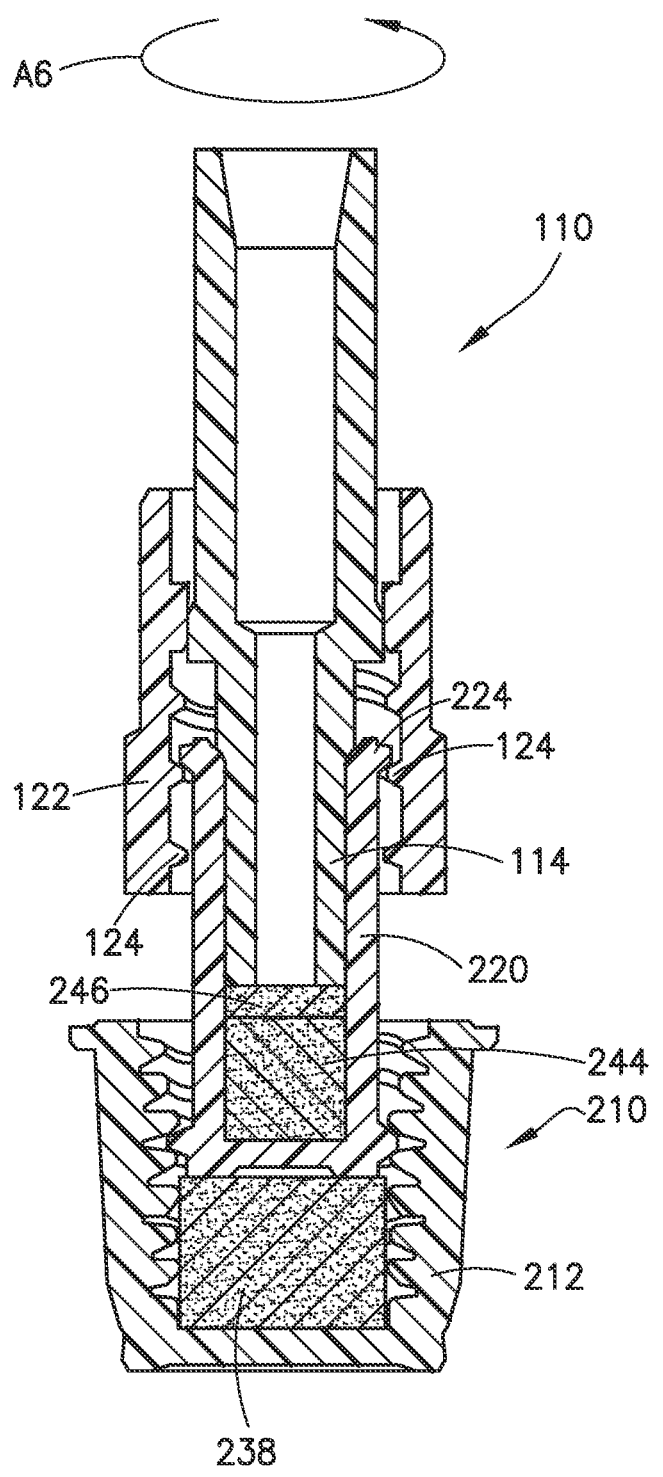
FIG. 5B is a cross-sectional view of the cap of FIG. 4A connected to a male connector, according to an aspect of the present disclosure.
Figure 5C:
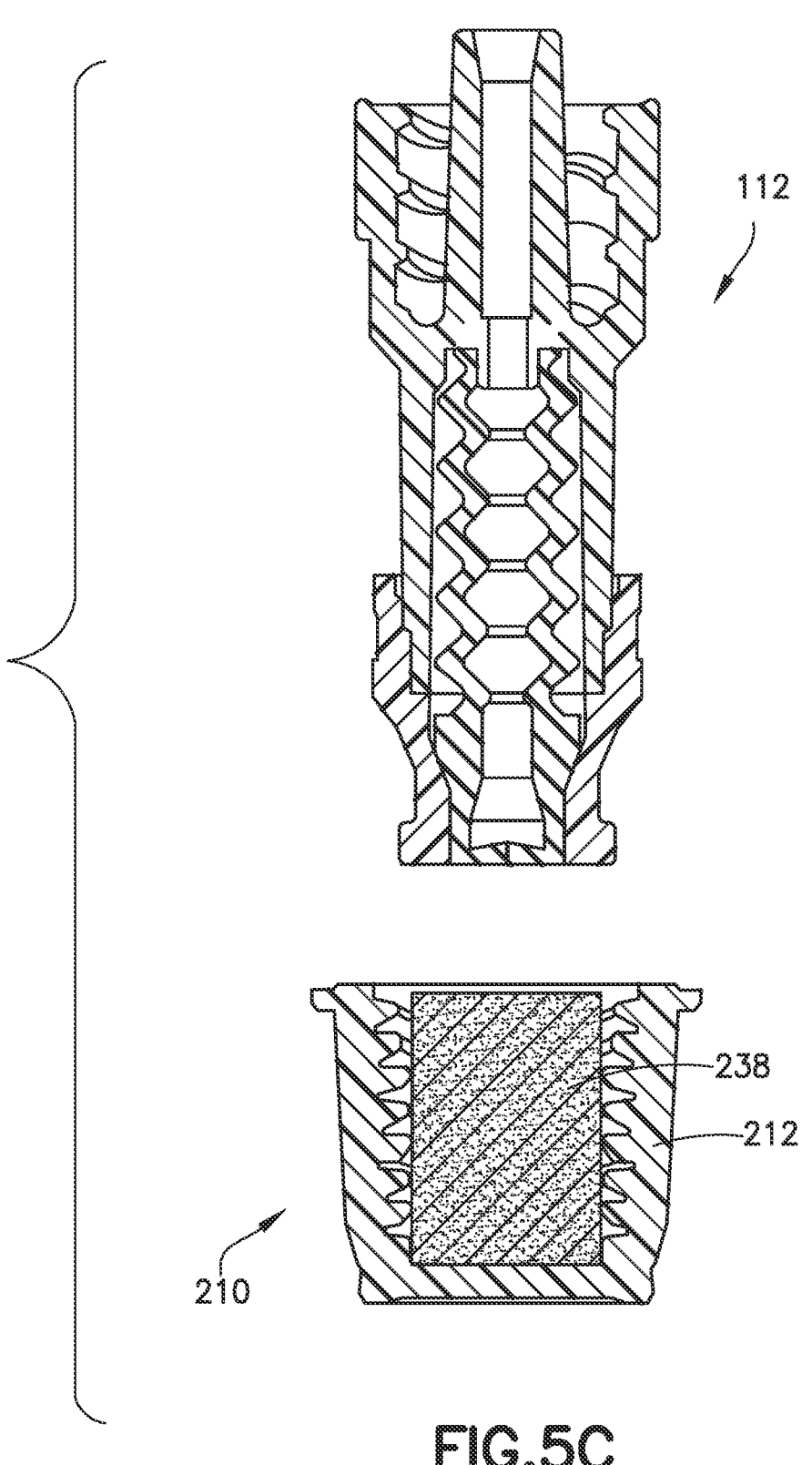
FIG. 5C is a cross-sectional view of the cap of FIG. 4A prior to being connected to a female luer connector, according to an aspect of the present disclosure.

The cap 210 differs from previous examples in the shape and configuration of the protective cover 250 and the inner housing 220. Specifically, as shown in FIGS. 4A-4C, the protective cover 250 is a rigid structure configured to maintain a molded shape. The protective cover 250 can include an open bottom 254, a closed top 256, and a sidewall 258 extending between the bottom 254 and the top 256. The sidewall 258 can be tapered toward the top 256 of the protective cover 250, as shown in FIGS. 4A and 4B. In some examples, the bottom 254 of the protective cover 250 includes a flange 260. A bottom surface of the flange 260 can be sealed to the top 216 of the outer housing 212.

When the protective cover 250 is sealed to the outer housing 212, the protective cover 250 defines an expanded interior of the cap 210, which is sized to receive an elongated inner housing 220. Specifically, as shown in FIGS. 4A-4C, the inner housing 220 is elongated, having an axial length L1 (shown in FIG. 4C), which is longer than in previous examples. As shown most clearly in FIG. 4B, a top portion of the elongated inner housing 220 protrudes through the open top 216 of the outer housing 212 and into the expanded space defined by the sidewall 258 of the protective cap 250.

The method of use for the cap 210 is similar to previous examples. In order to connect the cap 210 to a male connector 110 (shown in FIGS. 5A and 5B), the practitioner first removes the protective cover 250, as in previous examples. The practitioner then moves the male connector 110 toward the top 224 of the elongated inner housing 220 to insert the stem 114 of the male connector 110 into the inner housing 220. As previously described, the practitioner can also rotate the male connector 110 relative to the inner housing 220 causing the protrusions 252 or lugs of the inner housing 220 to engage the threads 124 of the shield 122 of the male connector 110. Once the male connector 110 is engaged to the elongated inner housing 220, the inner housing 220 can be removed from the outer housing 212. Specifically, the practitioner can rotate the inner housing 220 relative to the outer housing 212, as shown by arrow A6 (in FIG. 5B), causing the protrusion 252 or lug of the inner housing 220 to release from threads 236 of the outer housing 212. Once the outer housing 212 is removed, it can be discarded.

The cap 210 can be connected to a female connector 112 (shown in FIG. 5C) in the same way as in previous examples. Specifically, the practitioner first removes the protective cover 250 and inner housing 220 from the outer housing 212, as previously described. The practitioner then inserts the distal end portion 108 of the female connector 112 into the outer housing 212 by rotating the female connector 112 relative to the outer housing 212 causing the threads 236 of the outer housing 212 to engage the threads 128 of the female connector 112, as previously described.

While examples of the disinfecting cap 10, 210 and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:
1. A cap configured to engage a male connector and a female connector, comprising:
   a first housing for the female connector comprising a closed bottom, an open top, and a sidewall extending between the bottom and the top;

a first absorbent support disposed in the first housing configured to contact portions of the female connector;

a removable second housing for the male connector disposed in the first housing, the second housing comprising a bottom, a top, and a sidewall extending between the bottom and the top with an outer surface of the sidewall of the second housing engaged to an inner surface of the sidewall of the first housing, the second housing contacts and compresses the first absorbent support, when the second housing is removed from the first housing, the first absorbent support expands such that a top surface of the first absorbent support extends towards the open top of the first housing;

a second absorbent support disposed in the removable second housing configured to contact portions of the male connector; and a protective cover is removably mounted to the open top of the first housing by heat sealing, the protective cover is configured to protect the inner surface of the sidewall of the first housing, the outer surface of the second housing, and the first absorbent support and the second absorbent support.

2. The cap of claim 1, wherein the first housing is sized to engage the female connector to cover an opening of the female connector and the second housing is sized to engage the male connector to cover an opening of the male connector.

3. The cap of claim 1, configured such that, following removal of the second housing from the first housing, the first housing is sized for the female connector to engage an inner surface of the first housing, thereby securing the first housing to the female connector.

4. The cap of claim 1, wherein the male connector comprises a male luer connector comprising a stem configured to be inserted into the removable second housing, and wherein the second absorbent support is configured to clean and/or disinfect at least a distal tip of the stem.

5. The cap of claim 1, wherein the female connector comprises a female luer connector comprising a threaded outer surface that engages the inner surface of the sidewall of the first housing, and wherein the first absorbent support is configured to clean and/or disinfect the threaded outer surface of the female luer connector.

6. The cap of claim 5, wherein the inner surface of the sidewall of the first housing comprises threads that engage the threaded outer surface of the female luer connector.

7. The cap of claim 1, wherein the inner surface of the sidewall of the first housing comprises threads, and wherein the second housing comprises at least one protrusion extending radially outward from the sidewall of the second housing configured to engage the threads of the first housing to removably secure the second housing in the first housing.

8. The cap of claim 1, wherein the first housing and/or the second housing comprise single-molded parts, comprising a rigid thermoplastic polymer comprising at least one of polyester, polycarbonate, polypropylene, polyethylene, polyethylene terephthalate, or acrylonitrile butadiene styrene.

9. The cap of claim 1, wherein the first absorbent support and/or the second absorbent support comprise sponges and/or an open cell foam, including a porous foam comprising a thermoplastic elastomer.

10. The cap of claim 1, further comprising a cleaning or disinfecting solution absorbed by at least one of the first absorbent support and/or the second absorbent support, wherein the cleaning or disinfecting solution comprises Isopropyl Alcohol (IPA).

11. The cap of claim 10, wherein the cleaning solution comprises from about 0.5% to about 3.5% chlorhexidine gluconate and about 70% IPA.

12. The cap of claim 1, further comprising a seal disposed in the second housing between the second absorbent support and the top of the second housing, the seal covers the second absorbent support.

13. The cap of claim 12, wherein the seal comprises a thermoplastic elastomer, such as a closed cell foam formed from the thermoplastic elastomer.

14. The cap of claim 1, wherein the protective cover comprises an open bottom, a top, and a sidewall extending between the bottom and the top.

15. The cap of claim 1, wherein, when connected to the first housing, the removable second housing extends through the open top of the first housing, such that a portion of the second housing is disposed within a space defined by the sidewall of the cover.

16. The cap of claim 1, wherein the sidewall of the cover is tapered toward the top of the cover.

17. The cap of claim 1, wherein the bottom of the cover comprises a flange and wherein a bottom surface of the flange is sealed to the first housing.

* * * * *